United States Patent [19]
Tremulis

[11] Patent Number: 6,102,903
[45] Date of Patent: *Aug. 15, 2000

[54] DEVICE AND METHOD FOR SELECTIVELY DELIVERING FLUID INTO AN ANATOMICAL LUMEN

[75] Inventor: William S. Tremulis, Redwood City, Calif.

[73] Assignee: Medtronics, Inc., Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/572,821

[22] Filed: Dec. 14, 1995

[51] Int. Cl.⁷ ............................................. A61M 31/00
[52] U.S. Cl. ........................ 604/500; 604/249; 604/529
[58] Field of Search ................ 604/49, 93, 96–7, 604/164, 166–7, 249, 264, 280, 529, 256, 500, 507; 128/658, 772

[56] References Cited

U.S. PATENT DOCUMENTS

| | | | |
|---|---|---|---|
| 3,841,308 | 10/1974 | Tate | 604/249 |
| 4,413,989 | 11/1983 | Schjeldahl et al. | 604/96 |
| 4,543,087 | 9/1985 | Sommercorn et al. | . |
| 4,577,637 | 3/1986 | Mueller, Jr. | . |
| 4,661,094 | 4/1987 | Simpson | . |
| 4,813,934 | 3/1989 | Engelson et al. | . |
| 5,021,044 | 6/1991 | Sharkawy | 604/164 |
| 5,163,912 | 11/1992 | Gay et al. | 604/164 |
| 5,171,221 | 12/1992 | Samson | 604/167 |
| 5,209,728 | 5/1993 | Kraus et al. | . |
| 5,243,996 | 9/1993 | Hall | 604/164 |
| 5,250,034 | 10/1993 | Appling et al. | 604/249 |
| 5,256,144 | 10/1993 | Kraus et al. | 604/164 |
| 5,300,022 | 4/1994 | Klapper et al. | . |
| 5,334,154 | 8/1994 | Samson et al. | 604/96 |
| 5,378,237 | 1/1995 | Boussignac et al. | . |
| 5,496,294 | 3/1996 | Hergenrother et al. | . |
| 5,857,464 | 1/1999 | Desai | . |

FOREIGN PATENT DOCUMENTS

| | | |
|---|---|---|
| 3532885 | 3/1987 | Germany . |
| 9301856 | 2/1993 | WIPO . |
| 9408653 | 4/1994 | WIPO . |

*Primary Examiner*—Mark Bockelman

[57] ABSTRACT

An apparatus and method for selective delivering fluid into a fluid vessel is provided. In the method, a delivery catheter (2) is advanced over a guide wire (30) to a target location within fluid vessel, such as a restriction or blockage. After reaching the target location, therapeutic fluid is supplied under pressure into an axial lumen 12 of the delivery catheter. The fluid is inhibited from passing through the open distal end of the catheter so that the fluid will preferentially flow radially outward through a plurality of lateral infusion ports (20) in the delivery catheter. The guide wire may also be retracted into the catheter to deliver the fluid axially through the open distal end of the catheter.

16 Claims, 3 Drawing Sheets

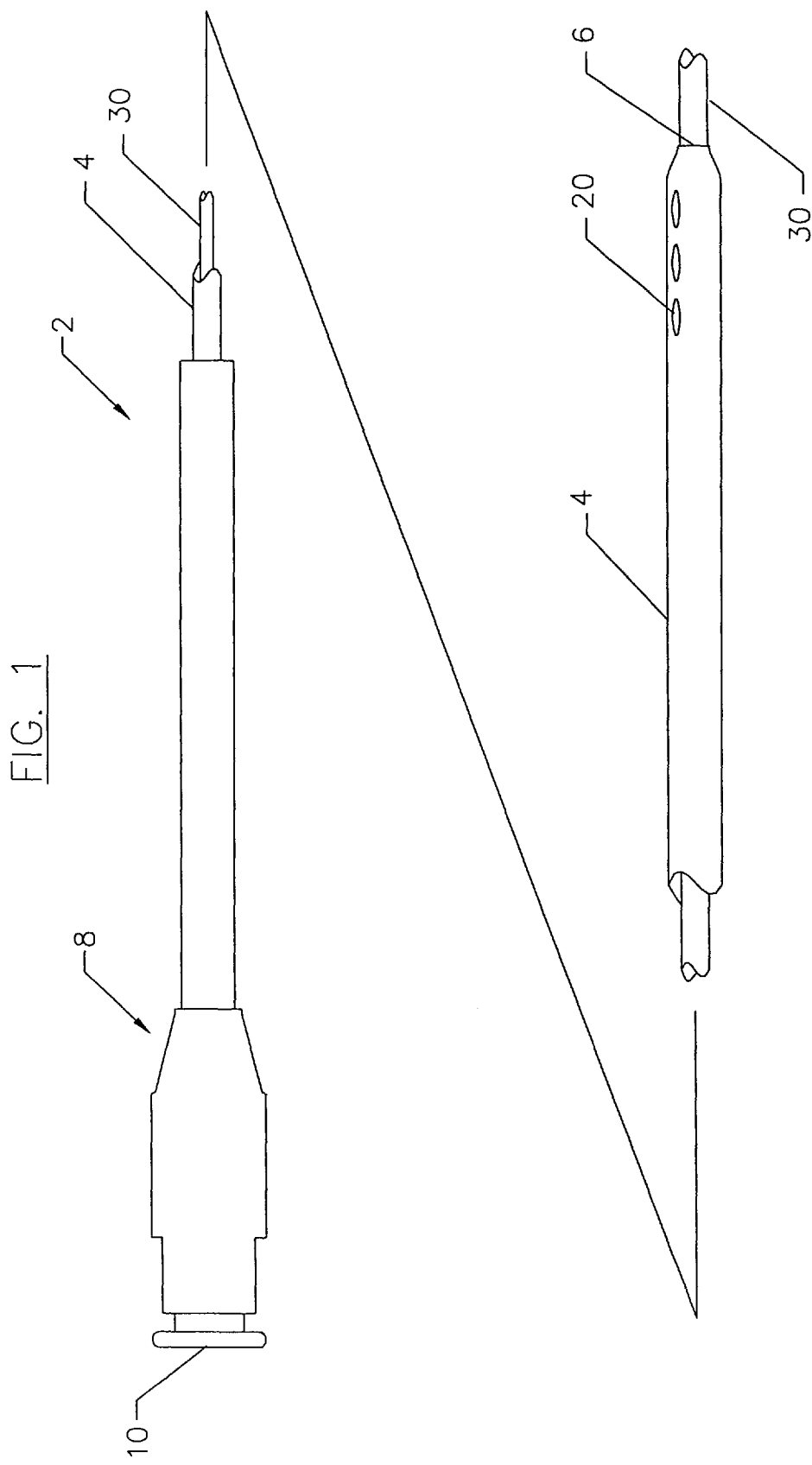

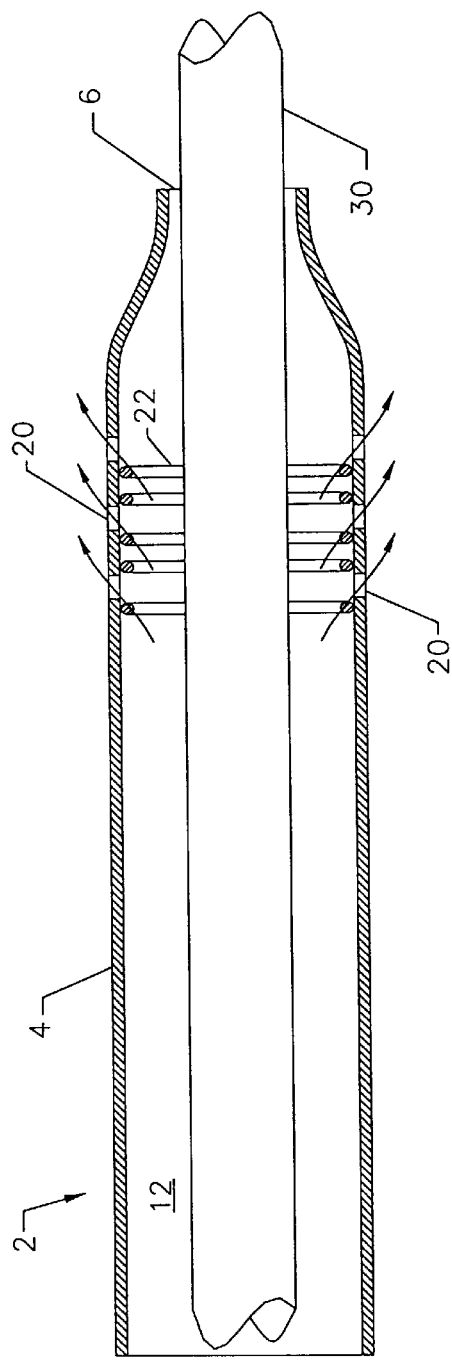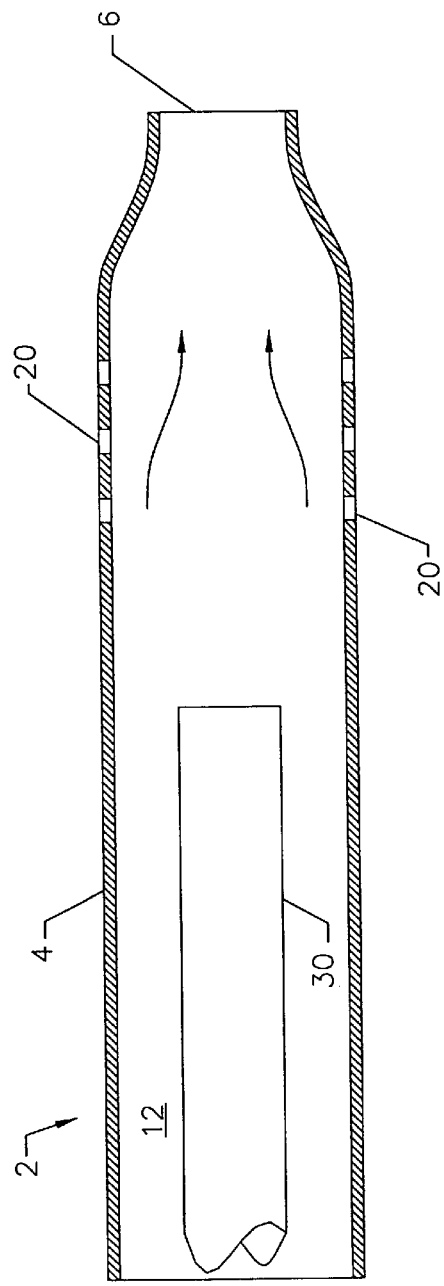

DEVICE AND METHOD FOR SELECTIVELY DELIVERING FLUID INTO AN ANATOMICAL LUMEN

BACKGROUND OF THE INVENTION

1. Field of the Invention

The present invention relates generally to the structure and use of medical catheters. More particularly, the present invention relates to the construction and use of an infusion or delivery catheter designed to selectively deliver fluid radially or axially into an anatomical lumen.

Delivery catheters are used for a variety of surgical applications, such as infusing therapeutic fluids into a desired location within a patient's vasculature. To position the delivery catheter into the target site, a guide wire is typically introduced percutaneously or through an open surgical incision and advanced to the target location within a fluid vessel. The delivery catheter is then introduced over the guide wire until the distal end of the catheter or a fluid delivering portion of the catheter reaches the target site. After reaching the target site, the therapeutic fluid is delivered through an axial lumen in the catheter and onto the target site through openings in the catheter body.

In many applications, it is often desirable to deliver the therapeutic fluid radially outward from the catheter directly onto the target site within the body lumen. For example, thrombolytic agents are often delivered onto a restriction or lesion in a blood vessel caused by a thrombosis or clot to lysis the clot and restore blood flow in the lumen. To accomplish this, lateral infusion ports are typically formed near the distal end of the catheter body for allowing fluid to flow radially outward from the axial lumen through the infusion ports to the surrounding blood vessel. Delivering the thrombolytic agents directly to the thrombosis results in faster lysis of the clot and restored blood flow in a shorter amount of time.

The need to radially deliver fluid through lateral infusion ports is problematic in delivery catheters intended for introduction into small body lumens over guide wires. Existing catheters typically have distal guide wire ports in communication with the axial lumen of the catheter body for allowing the catheter to be advanced over the guide wire. Unfortunately, the momentum of the fluid flowing through the axial lumen and the relatively small size of the radially disposed infusion ports often causes a substantial portion of the fluid to flow past these infusion ports, where it is discharged axially through the guide wire port. In addition, the restriction or lesion in the blood vessel may often cover or partially restrict flow through the infusion ports, which increases the difficulty of delivering fluid through these radially disposed ports. The fluid delivered through the guide wire port is typically wasted downstream of the blockage, which may increase the time required to treat the lesion and restore the blood flow through the vessel.

For these and other reasons, it would be desirable to provide improved catheters and methods for infusing fluids onto target sites within anatomical lumens. These catheters and methods should be capable of delivering fluid flow radially outward through infusion ports directly onto, for example, a restriction or lesion in a blood vessel. In particular, these catheters should be capable of delivering the fluid through the infusion ports when the lesion partially covers or otherwise inhibits fluid flow through these ports.

2. Description of the Background Art

U.S. Pat. No. 4,661,094 describes a perfusion catheter having an inner tube which receives a guide wire for advancing the catheter through a body lumen. The catheter has a plurality of longitudinally spaced holes for permitting the flow of liquid from and into the flow passage through the holes when the catheter is positioned in a lesion or restriction within the body lumen. U.S. Pat. No. 5,334,154 describes a balloon angioplasty catheter having lateral perfusion ports in the catheter body. The perfusion ports have inwardly depressed proximal edges for preventing the excursion of a guide wire inserted into the catheter through the perfusion ports. U.S. Pat. No. 5,318,529 describes an angioplasty balloon catheter having a guide wire tube which receives a guide wire permanently received in an inflation lumen of the catheter. The guide tube has a very close tolerance over the guide wire, preferably below 0.0005 inch, and is optionally filled with a thixotropic material or elastomeric seal to prevent blood seepage and loss of inflation medium. Other drug infusion catheters having lateral ports include U.S. Pat. Nos. 5,209,728, 5,021,044, 4,543,087 and 5,300,022 and PCT application No. WO 094/08653.

A balloon catheter having a single lumen for both inflation and receiving a guide wire is described in co-pending application Ser. No. 08/415,002, filed on Mar. 31, 1995, naming William Tremulis as inventor. The full disclosure of the co-pending application is incorporated herein by reference. Other patents disclosing balloon catheters having guide wire and inflation lumens in different combinations include U.S. Pat. Nos. 4,413,989, 5,380,282, 5,378,237, 5,364,347, 5,330,428, 5,312,340, 5,246,420 and 5,201,754.

SUMMARY OF THE INVENTION

According to a method of the present invention, a delivery catheter is positioned over a flow restrictor at a target location within a body lumen of a patient such that the flow restrictor extends into a distal port at a distal end of the delivery catheter. After reaching the target location, a therapeutic or diagnostic fluid, such as a thrombolytic agent, is supplied under pressure into an inner lumen of the delivery catheter. While the flow restrictor is present in the distal port, fluid is restricted or inhibited from flowing through the port so that at least a portion of the fluid preferentially flows radially outward through one or more lateral infusion ports in the delivery catheter. In this manner, the fluid is applied directly to the target site, e.g., a restriction or lesion in a blood vessel, to increase the speed and efficiency of the process. By withdrawing the flow restrictor from the distal port, conversely, the fluid can be delivered through the distal port, with the relative amounts passing through the distal and lateral ports depending on their relative flow resistances and areas.

The flow restrictor will preferably be a guide wire, which can be used to axially guide the delivery catheter into the target location. A distal guide wire port on the delivery catheter will usually have a reduced diameter (i.e., smaller than the lumen diameter) to form an annular restrictive passage between the inner peripheral wall of the port and the outer surface of the guide wire. The annular restrictive passage offers a greater resistance to flow than the lateral infusion ports (i.e., the flow area afforded by the annular passage is much less than the total area of the lateral passages) so that a substantial portion of the fluid within the inner lumen of the catheter body will preferentially flow through the lateral infusion ports, usually, at least 50%, more usually 90%. Thus, a therapeutic or diagnostic fluid may be radially delivered directly to a restriction or blockage in a vessel even when the blockage may cover or partially inhibit flow through the lateral infusion ports. This radial flow delivery may result in faster and more efficient lysis of a clot because most of the therapeutic fluid flows directly onto the clot; rather than through the open distal end of the catheter, where it would be wasted downstream of the blockage.

The method of the present invention may further include decreasing the flow resistance offered by the annular restrictive passage such that the fluid preferentially flows axially through the open distal end. This may be accomplished by positioning the distal end of the catheter over a reduced diameter portion of the guide wire or by proximally retracting the guide wire so that it does not extend through the distal end of the catheter. The distal guide wire port is sized so that significantly more fluid will flow through the distal open end of the catheter than through the infusion ports when the guide-wire does not extend through the guide wire port.

A delivery catheter according to the present invention is intended for use in combination with a separate, movable guide wire of the type commonly used in medical procedures, particularly intravascular procedures. The delivery catheter includes a catheter body having a distal end, a proximal end and an inner lumen therebetween. A guide wire port is formed at the distal end of the inner lumen and a plurality of lateral infusion ports are formed in the catheter body in communication with the inner lumen. The guide wire port has a reduced cross-sectional area such that, when the guide wire extends through the guide wire port, the port offers a greater resistance to flow than the lateral infusion ports. With this configuration, a substantial portion of the fluid will flow through the lateral infusion ports directly to the target site when the guide wire extends through the guide wire port.

Conversely, the guide wire port is sized to offer less resistance to flow than the lateral infusion ports when the guide wire is not extending through the guide wire port. Thus, a substantial portion of the fluid will flow axially through the guide wire port when the guide wire has been retracted into the catheter body. This allows the operator to selectively deliver flow radially through the lateral infusion ports or axially through the distal guide wire port simply by translating the guide wire relative to the catheter body.

Other features and advantages of the invention will appear from the following description in which the preferred embodiment has been set forth in detail in conjunction with the accompanying drawings.

BRIEF DESCRIPTION OF THE DRAWINGS

FIG. 1 is a side elevational view of a delivery catheter constructed in accordance with the principles of the present invention, shown introduced over a separate guide wire;

FIG. 2 is a detailed sectional view of the distal end of the delivery catheter of FIG. 1, illustrating radial infusion of fluid through lateral infusion ports in the delivery catheter;

FIG. 3 is a detailed sectional view of the distal end of the delivery catheter of FIG. 1, illustrating axial infusion of fluid through a distal guide wire port in the delivery catheter.

DESCRIPTION OF THE SPECIFIC EMBODIMENTS

Figure 4:
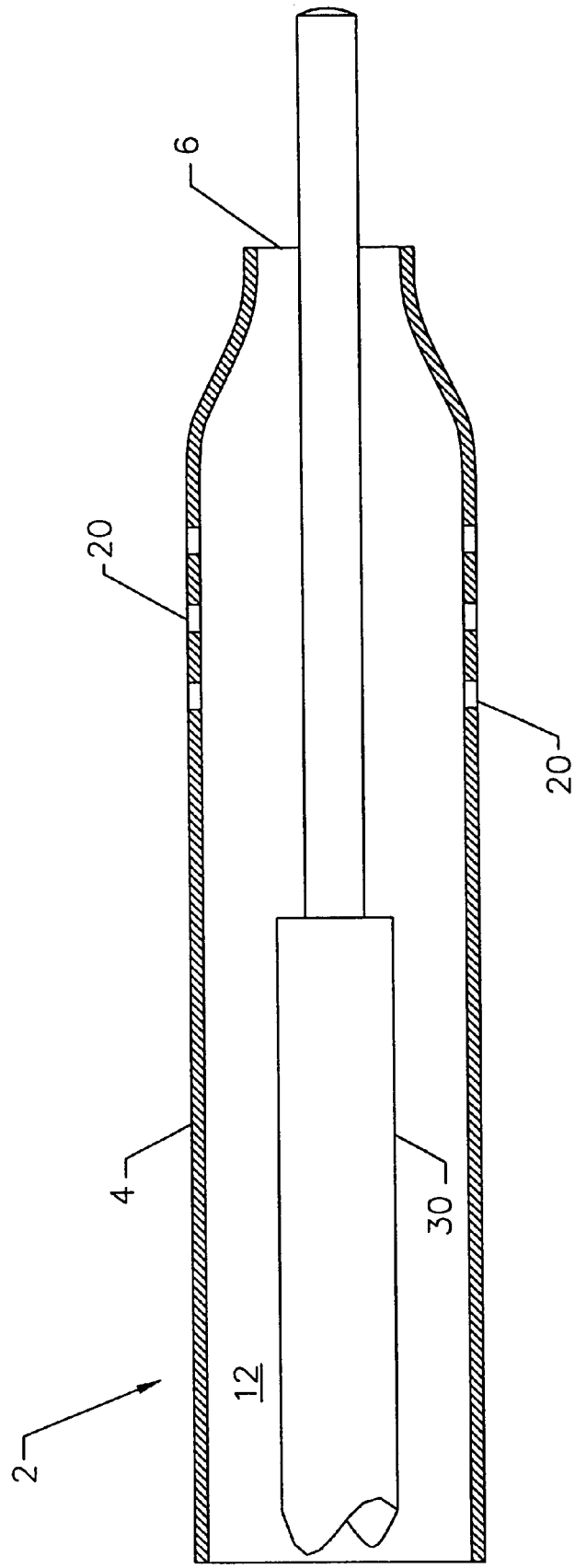
FIG. 4 illustrates a guidewire with a reduced diameter portion within the annular restrictive passage defined by the guidewire port of the catherter system.

The present invention provides both a delivery catheter and a method for selectively delivering fluid to a target site within a body lumen. The catheter may be used to deliver therapeutic fluids, e.g., thrombolytic, fibrinolytic, anti-thrombolytic, and anti-restonic agents, as well as diagnostic agents, e.g., contrast media, and the target site will usually be a region within a patient's vasculature, e.g., a stenotic region, aneurysm, or the like. It will be appreciated, however, that the design and method could be used with a variety of other medical catheters where the ability to selectively deliver fluid radially and axially into a body lumen is advantageous.

The delivery catheter of the present invention will comprise a catheter body having a proximal end, a distal end and an inner lumen extending therebetween. The dimensions, materials, and construction of the catheter body may vary widely and will depend on the particular application intended for the catheter. In the case of therapeutic fluid delivery into vascular regions, the catheter body will typically have a length of 10 to 175 cm, usually 60 to 150 cm. The outside diameter of the catheter body will typically be in the range from 1 to 12 F (1 F (French) equals 0.33 mm). Usually, the proximal end portion of the catheter body will range from 1.5 to 10 F and the distal end portion will range from 1 to 5 F.

The catheter body will usually be formed by extrusion of an organic polymer, such as polyethylenes, polyvinylchlorides, polyurethanes, polyesters, polytetrafluoroethylenes (PTFE), and the like. Optionally, the catheter body may be formed as a composite having a reinforcement material incorporated within the polymeric body in order to enhance its strength, flexibility and toughness. Suitable reinforcement layers include braiding, wire mesh layers, and the like. The catheter body will typically be formed with at least one continuous lumen extending from the proximal end to the distal end being provided for both fluid delivery and guide wire-receiving functions. Of course, the catheter body may include additional lumens for delivery of the fluid so long as the additional lumens are in communication with the guide wire-receiving lumen at the distal end of the catheter, as described in greater detail below.

A proximal hub will normally be provided at the proximal end of the catheter body. The hub will serve to provide access to the delivery/guide wire lumen, typically including at least one port. The port will be adapted for receiving the guide wire and for connection to a source of therapeutic or diagnostic fluid. Alternatively, the hub may include first and second separate ports for these functions. The construction of such hubs and connection ports is conventional. For example, the hub may be coupled to a Y-shaped rotating hemostatic valve for providing both the guide wire and fluid delivery functions.

A guide wire port will be provided at the distal end of the catheter body for axial translation of the catheter over the guide wire and for axially delivering fluid to a target site. The guide wire port will have dimensions selected to restrict axial flow of fluid through the guide wire port when the guide wire extends through the guide wire port and to allow relatively free flow of the fluid therethrough when the guide wire is withdrawn from the catheter. The guide wire port is preferably provided by forming a tapered conical distal tip on the catheter body that tapers inwardly to a circular distal opening. The circular opening forms an annular restrictive passage between the distal tip and the guide wire when the guide wire extends therethrough.

One or more lateral infusion port(s) will be provided near the distal end of the catheter body for radially delivering the fluid from the inner lumen to the target site. Usually, a plurality of infusion ports will be distributed over the catheter body in a predesignated pattern, more usually the ports will be longitudinally and circumferentially spaced from each other about the catheter body. The number of ports and the spacing between adjacent ports will, of course, depend on a variety of factors, such as the function of the delivery catheter, the type and quantity of fluid being delivered, the size of the restriction or blockage, etc. For example, the catheter may have from 1 to 100 ports, usually from 3 to 30 ports, and the ports may be formed on only one side of the catheter body to specifically direct fluid towards one side of a fluid vessel. Alternatively, the catheter may have a multitude of tiny perforations (i.e., greater than 100) or the catheter may have a portion constructed of a porous material.

The lateral infusion ports will have dimensions selected so that the ports offer less resistance to flow than the guide wire port when the guide wire extends through the guide wire port and a greater resistance to flow when the guide wire does not extend through the guide wire port. The annular flow area through the guide wire port is determined by the peripheral diameter of the port and the outer diameter of the separate guide wire. Typically, the difference between these diameters will be in the range from 0.01 to 0.5 mm, preferably being in the range from 0.05 to 0.1 mm. For conventional guide wire diameters, the annular flow area will typically be 0.005 to 0.5 mm$^2$ and preferably 0.01 to 0.3 mm$^2$. The lateral ports will usually have a total area in the range from 0.01 to 0.5 mm$^2$ more usually from 0.025 to 0.25 mm$^2$.

The guide wire will usually be a conventional guide wire having a length sufficient to extend through a body lumen beyond the target site, e.g., a stenotic region. The guide wire may include a reduced diameter portion near the distal end of the guide wire. The reduced diameter portion will have dimensions, (i.e., length and cross-sectional area or diameter) selected to allow fluid to preferentially flow through the guide wire port when the guide wire is positioned such that the reduced diameter portion resides within the guide wire port. The guidewire port will typically have a diameter in the range of about 0.25 to 2.0 mm. The difference between the diameter of the reduced portion and the remainder of the guide wire will typically be from 0.01 to 0.4 mm, more usually from 0.02 to 0.20 mm.

Referring now to FIGS. 1–3, a delivery catheter 2 comprises a catheter body 4 having a guide wire port 6 at its distal end and a proximal hub 8 at its proximal end. The hub includes a guide wire/fluid delivery port 10 which communicates with an axial lumen 12 (FIG. 2) extending fully between proximal hub 8 and guide wire port 6.

Referring in particular to FIGS. 2 and 3, the distal end portion of catheter body 4 defines a number of lateral infusion ports 20 spaced longitudinally and circumferentially about body 4. A coil 22 (FIG. 2) extends through the distal end portion of axial lumen 12 between infusion ports 20 to facilitate location of the ports with a fluoroscope or the like during the surgical procedure.

The delivery catheter 2 is introduced over the separate, movable guide wire 30 in a conventional manner. Usually, catheter 2 will be loaded over the proximal end of guide wire 30, after the guide wire 30 has been positioned within the target body lumen. The delivery catheter 2 may then be advanced over the guide wire so that catheter 2 also reaches the target location.

If radial delivery of the fluid is desired, guide wire 30 will extend beyond the target location so that the guide wire extends through guide wire port 6 of catheter 2, as shown in FIG. 2. The fluid is then introduced via conventional means into axial lumen 12, where a substantial portion of the fluid is delivered through lateral infusion ports 20 to the target location. If axial delivery of the fluid is desired, guide wire 30 is retracted into axial lumen 12 proximal of infusion ports 20, as shown in FIG. 3. The majority of the fluid introduced into the lumen 12 will bypass infusion ports 20 and flow directly through guide wire port 6 into the body lumen.

Although the foregoing invention has been described in detail for purposes of clarity of understanding, it will be obvious that certain modifications may be practiced within the scope of the appended claims. For example, the restrictive passage between the guide wire and the distal end of the catheter may be formed in a variety of manners other than that described above and illustrated in the figures. The distal end of the catheter may, e.g., include an annular insert that reduces the cross-sectional area of the opening. In addition, the guide wire may have an increased diameter portion that can be aligned with the open distal end of the catheter when radial fluid flow is desired.

Alternatively, fluid flow through the distal guide wire port may be restricted by a flow restrictor other than a guide wire. For example, once the delivery catheter is in position at the target location, the guide wire may be removed and replaced with a flow restrictor or occlusion device, such as a valve wire, that extends into the guide wire port to inhibit flow therethrough.

What is claimed is:

1. A method for preferentially infusing a fluid through distal and lateral ports of a delivery catheter comprising:

positioning the delivery catheter over a flow restrictor at a target location within a body lumen of a patient such that the flow restrictor extends into a distal port of the delivery catheter and forms a restrictive annular passage between an inner peripheral wall of the distal port and an outer surface of the flow restrictor, wherein said positioning step comprises fluoroscopically observing a coil in the distal end of the catheter and position in at least one lateral diffusion port in the catheter based on the observed position of the coil said flow restrictor having a distal tip that is entirely retractable into the coil; and supplying fluid into a lumen of the delivery catheter wherein the lumen terminates at the distal port and fluid flow through the distal port is substantially inhibited but not stopped by the flow restrictor and fluid preferentially flows radially outward through the at least one lateral infusion port in the delivery catheter.

2. The method of claim 1 wherein the flow restrictor extends through the distal port to a position distal of the delivery catheter.

3. The method of claim 1 wherein the flow restrictor is a guide wire.

4. The method of claim 1 wherein the delivery catherter is positioned within a blood vessel.

5. The method of claim 1 wherein the supplying step is carried out with thrombolytic agents.

6. The method of claim 1 wherein the fluid flows radially through a plurality of lateral infusion ports longitudinally and circumferentially spaced from each other.

7. The method of claim 1 further comprising the step of decreasing the flow resistance offered by the annular restrictive passage such that the fluid preferentially flows axially through the open distal end.

8. The method of claim 7 wherein the decreasing the flow resistance step comprises axially translating the delivery catheter relative to the guide wire such that the guide wire is proximally spaced from the distal end of the delivery catheter to thereby increase a cross-sectional area of the guide wire port.

9. A method for selectively infusing a fluid through a delivery catheter comprising:

positioning the delivery catheter over a flow restrictor at a target location within a body lumen of a patient such that the flow restrictor extends into a distal port of the delivery catheter and forms a restrictive passage between an inner peripheral wall of the distal port and an outer surface of the flow restrictor, wherein said positioning step comprises fluoroscopically observing a coil in the distal end of the catheter and positioning at least one lateral diffusion port in the catheter based on the observed position of the coil said flow restrictor having a distal tip that is entirely retractable into the coil;

supplying fluid into a lumen of the delivery catheter wherein the lumen terminates at the distal port and fluid flow through the distal port is substantially inhibited by the flow restrictor and fluid preferentially flows radially outward through the at least one lateral infusion port in the delivery catheter; and decreasing the flow resistance offered by the annular restrictive passage such that the fluid preferentially flows axially through the open distal end;

wherein the decreasing the flow resistance step comprises axially translating the delivery catheter relative to the guide wire to align the distal end of the delivery catheter with a reduced diameter portion of the guide wire to thereby increase a cross-sectional area of the annular restrictive passage.

10. A delivery catheter system comprising:

a movable guide wire having a distal tie;

a delivery catheter having a distal end, a proximal end and an inner lumen extending between said ends and sized for receiving at least a portion of the guide wire, the catheter body defining a guide wire port at the distal end of the inner lumen, and a plurality of patent lateral infusion ports; and a fluoroscopically observable coil in the distal end of the delivery catheter wherein turns of the coil are positioned between the lateral infusion ports, the entire guidewire tip being retractable into the coil:

wherein the guide wire port and the guide wire define a restrictive passage therebetween, the restrictive passage offering a greater resistance to flow than the lateral infusion ports.

11. The delivery catheter system of claim 10 wherein the guide wire port offers less resistance to flow than the lateral infusion port when the guide wire is not extending through the guide wire port.

12. The delivery catheter system of claim 10 wherein the guide wire port has a cross-sectional area substantially smaller than an inner diameter of the delivery catheter.

13. The delivery catheter system of claim 10 wherein the catheter body defines a plurality of lateral infusion ports longitudinally and circumferentially spaced from each other and communicating the inner lumen with an outer surface of the catheter body.

14. The delivery catheter system of claim 10 wherein the lateral infusion ports each have a cross-sectional area of 0.01 to 0.5 mm2.

15. The delivery catheter system of claim 10 wherein the guide wire port has a diameter of 0.25 to 2.0 mm.

16. The delivery catheter system of claim 10 wherein the guide wire port has a diameter which provides an annular clearance over the guide wire in the range from 0.02 to 0.5 mm.

* * * * *